United States Patent [19]
Pellegrino et al.

[11] Patent Number: 5,425,069
[45] Date of Patent: Jun. 13, 1995

[54] MOBILE X-RAY APPARATUS

[75] Inventors: Anthony J. Pellegrino, New Fairfield, Conn.; Kenneth F. Defreitas, Patterson, N.Y.; Daniel N. Lyke, New Milford, Conn.; Richard F. Schutz, Brewster, N.Y.

[73] Assignee: Lorad Corporation, Danbury, Conn.

[21] Appl. No.: 158,625

[22] Filed: Nov. 26, 1993

[51] Int. Cl.⁶ .............................................. H05G 1/02
[52] U.S. Cl. ..................................... 378/198; 378/193; 378/197
[58] Field of Search ............... 378/193, 197, 198, 196, 378/204, 102

[56] References Cited

U.S. PATENT DOCUMENTS

| | | | |
|---|---|---|---|
| 2,051,508 | 8/1936 | Wildeboer | 378/198 X |
| 2,113,866 | 4/1938 | Thwaites | 378/198 X |
| 2,556,909 | 6/1951 | Feibel et al. | 378/198 X |
| 2,846,587 | 8/1958 | Thurow | 378/197 |
| 3,025,401 | 3/1962 | Lauterbach | 378/197 X |
| 3,644,735 | 2/1972 | Vandervelden | 378/197 X |
| 3,702,935 | 11/1972 | Carey et al. | |
| 3,790,805 | 2/1974 | Foderaro | |
| 3,801,790 | 4/1974 | Götzl et al. | 378/198 |
| 4,113,042 | 9/1978 | Vaill | |
| 4,166,602 | 9/1979 | Nilsen et al. | 378/197 X |
| 4,322,623 | 3/1982 | Grady | |
| 4,326,131 | 4/1982 | Waerve | |
| 4,387,468 | 6/1983 | Fenne et al. | |
| 4,590,378 | 5/1986 | Platz | |
| 4,646,862 | 3/1987 | Meili | |
| 4,697,661 | 10/1987 | Pajerski et al. | |
| 4,752,948 | 6/1988 | MacMahon | |
| 4,989,229 | 1/1991 | Negrelli et al. | |
| 5,008,921 | 4/1991 | Kaul et al. | |
| 5,067,145 | 11/1991 | Siczek et al. | |
| 5,081,662 | 1/1992 | Warden et al. | |

OTHER PUBLICATIONS

Kramex SCD-125 Condenser Discharge Mobile X-Ray Unit, No date.
Kramex SCD-105 Condenser Discharge Mobile X-Ray Unit, No Date.
Kramex Model SCD-125 Mobile X-Ray Unit . . . , No Date.
Kramex Model: SCD-105 Mobile X-Ray Unit . . . , No Date.
Shimadzu Medical Systems Brochure, MC125L-50, Cordless Mobile X-Ray, No Date.
Picker Explorer, Setting New Standards In Mobile X-Ray Performance, No Date.
Picker Explorer II Mobile X-Ray System, 1989, GE Medical Systems AMX-4 Mobile X-Ray System, 1987.

*Primary Examiner*—David P. Porta
*Attorney, Agent, or Firm*—Ware, Fressola, Van Der Sluys & Adolphson

[57] ABSTRACT

An improved mobile X-ray unit has a counterweighted articulating X-ray tube support arm that allows positioning of an attached X-ray tube virtually without the need for moving a supporting carriage. The improved mobile X-ray unit also allows the X-ray tube to be locked to the supporting carriage during travel and the articulating X-ray arm includes several electro-magnetically actuated disk brakes capable of locking the articulating X-ray arm in a predetermined position. In the event that the carriage movement is required, the carriage may be moved by application of force on a force sensing handle engaged with the carriage by two strain gage assemblies. The strain gage assemblies provide signals to a motor drive control circuits which in turn propel two driven wheels in the direction and proportional to the force applied to the handle relative to the carriage.

7 Claims, 8 Drawing Sheets

MOBILE X-RAY APPARATUS

BACKGROUND OF THE INVENTION

1. Field of the Invention

The present invention generally relates to mobile x-ray apparatus, and more particularly to an improved mobile x-ray apparatus for obtaining radiographs of bed-ridden patients in hospitals, nursing homes or in other similar situations where the equipment must be brought to the patient.

2. Description of the Prior Art

Mobile x-ray apparatus for taking radiographic images of a bed-ridden patient in the patient's hospital room are well known. Such apparatus are particularly beneficial in situations where the risks of moving the patient to stationary radiography apparatus is great. Given the inherent advantages of mobile X-ray apparatus in such situations, the demand for mobile x-ray apparatus is growing and as such there are many mobile X-ray apparatus offered by a variety of manufacturers for taking such X-rays.

The apparatus offered by these manufacturers generally have a large carriage that holds a significant number of heavy lead acid batteries used to power the X-ray tube. Thus, movement of the carriage tends to be awkward due to its large size and heavy weight. Controlled motor drive systems have been used to facilitate movement of the carriage both from the place where the mobile X-ray unit is stored to the location patient in need as well as fine movement often needed to position the X-ray tube over the area of the patient to be radiographed. Whether moving the apparatus forward or backward with the motor control system, it is desirable to have a motor control system that provides the operator with a responsiveness that most nearly simulates the responsiveness of a shopping cart to the operator's touch. Prior art apparatus have generally failed to provide simple, inexpensive, reliable and responsive drive systems.

It is also desirable to provide a mobile X-ray apparatus in which the X-ray tube is essentially positionable over the entire bed-ridden patient without the need for moving the cart. Although the prior art offer telescoping and rotating X-ray tube support arms, the prior art apparatus generally fail to provide a system wherein the X-ray tube may be positioned over the patient without the need for moving the cart. Positioning the X-ray tube by moving the cart can be awkward and often frustrating at times for the operator who needs to precisely position the X-ray tube over a particular part of the patient.

SUMMARY OF THE INVENTION

Accordingly, it is one object of the present invention to provide an improved mobile X-ray apparatus for taking radiographs of patients having medical conditions where it is more prudent to bring the apparatus to the patient than the patient to the apparatus.

This object is accomplished, at least in part, by the provision of a mobile X-ray apparatus having an articulating X-ray tube support arm, formed from a plurality of pivoting support appendages, for supporting and placing the X-ray tube in a predetermined position to take a radiograph of a patient.

This object is also accomplished, at least in part, by the provision of a mobile X-ray apparatus having a mast for supporting an X-ray tube support arm, the mast being formed so as to have flanges connected by a web and a pair of rails on each side of the web where the X-ray tube support arm and a counterweight may be slidably engaged.

The object is further accomplished, at least in part, by the provision of a mobile X-ray apparatus having a handle connected to the carriage of the apparatus by two strain gages at the ends thereof, where the strain gages provide electrical signals indicating the direction and degree of force placed on the handle relative to the carriage, a plurality of driven wheels, and a means for controlling the direction and magnitude of rotation of the driven wheels based on the electrical signals provided by the strain gages, Other objects and advantages of the present invention will become apparent to those skilled in the art from the following detailed description read in conjunction with the attached drawings and claims appended hereto.

BRIEF DESCRIPTION OF THE DRAWINGS

The drawings, not drawn to scale, include.

DETAILED DESCRIPTION OF THE INVENTION

Figure 1:
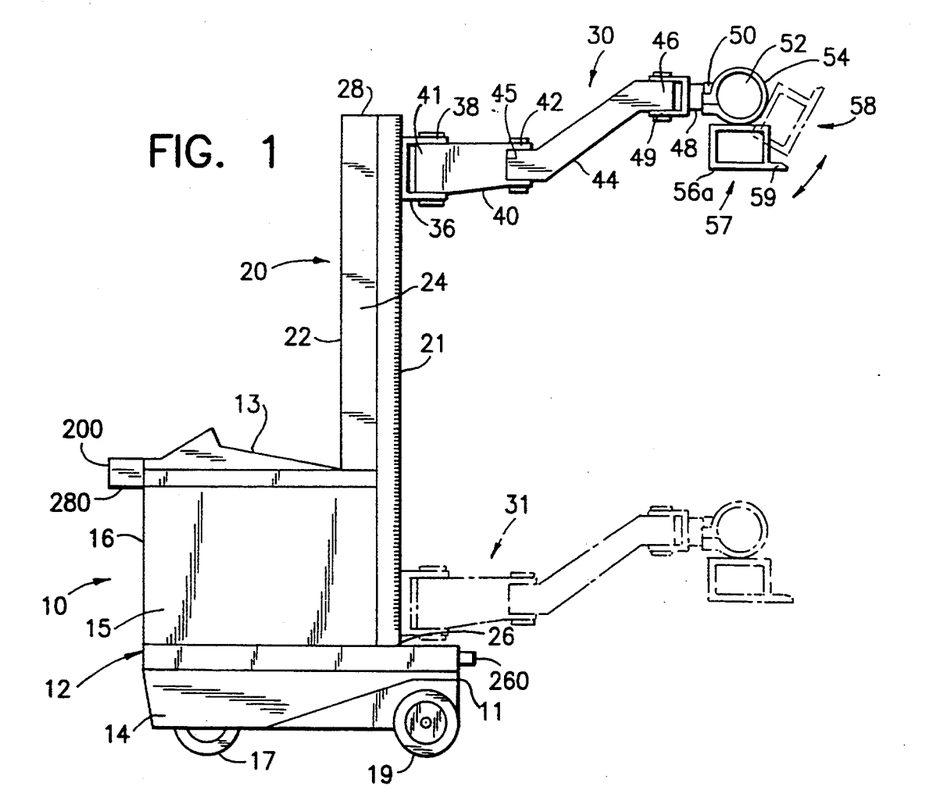
FIG. 1 which is a side view of the improved mobile X-ray apparatus principally illustrating the mast and the articulating X-ray tube support arm, and the movement of the arm along mast.
Figures 2A, 2B:
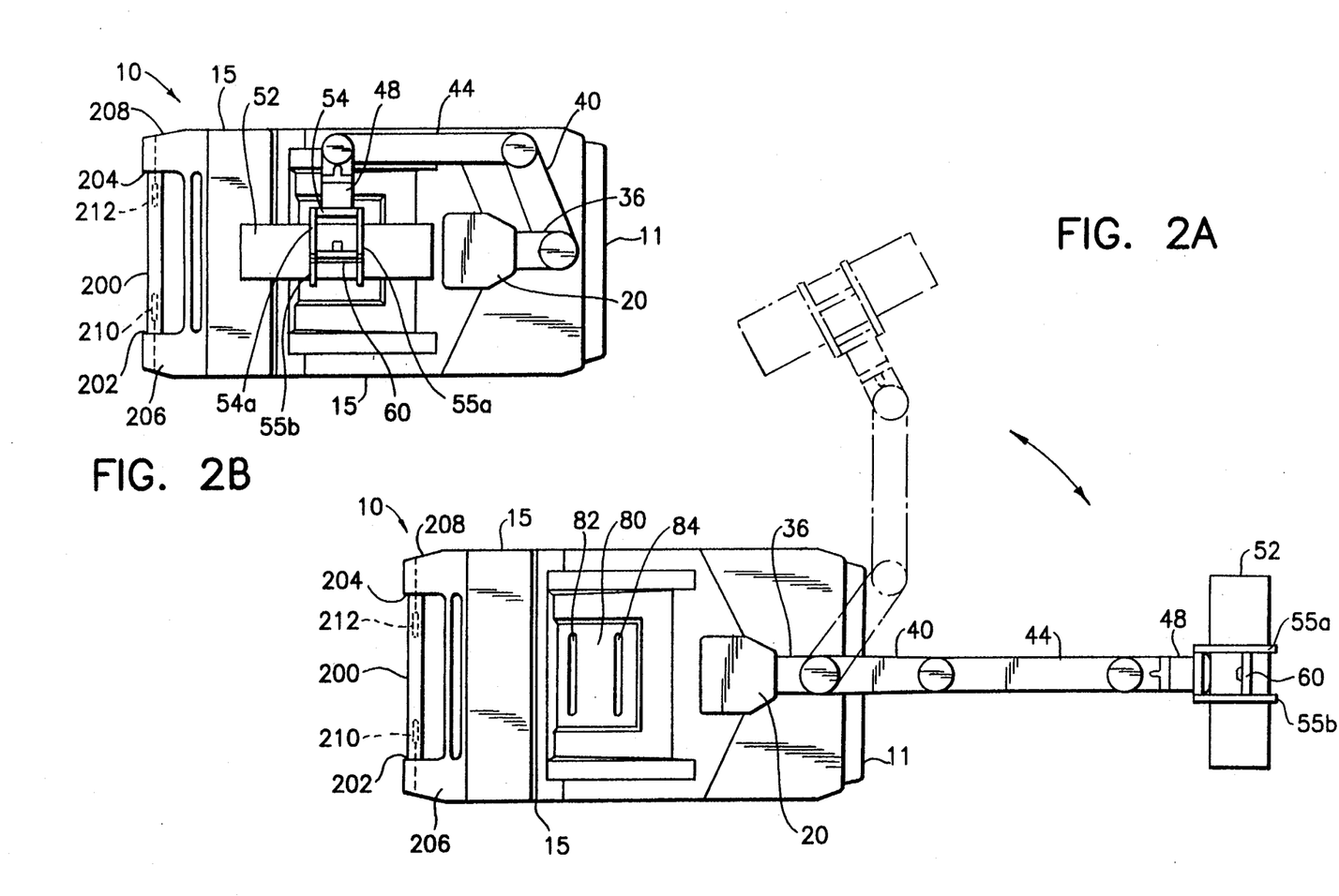
FIG. 2A which is a top view of the improved mobile X-ray apparatus principally illustrating the pivotable movement of the articulating X-ray tube support arm.
FIG. 2B which is a top view of the improved mobile X-ray apparatus principally illustrating the storage of the X-ray tube and articulating X-ray tube support arm for movement of the apparatus from one location to another.

Referring to FIGS. 1, 2A and 2B, a mobile X-ray unit is generally indicated by the numeral 10. The mobile X-ray unit 10 includes a carriage 12 having a front portion 11, a top 13, a base 14, two opposed sides 15 and a rear portion 16. The base 14 is supported from the ground by a plurality of wheels comprising a pair of rear driven wheels and a pair of front wheels. Right rear driven wheel 17 and right front wheel 19 illustrated in FIG. 1 and a complimentary left hand side pair of wheels (not shown) provide stable support for the carriage 12.

The mobile X-ray unit 10 further includes a mast as generally indicated by the number 20. The mast has a front side 21, a rear side 22, two opposed sides 24, a first end 26 and a second end 28. Attached to the mast 20 is an articulating X-ray tube support arm shown in a fully raised position as generally indicated by the numeral 30. The articulating X-ray tube support arm 30 is slidable along substantially the entire length of the mast 20. A fully lowered illustration of the articulating X-ray tube support arm 30 is shown in phantom in FIG. 1 and its fully lowered position is generally indicated by the numeral 31.

The articulating X-ray tube support arm 30 features a plurality of coupled pivotable support appendages that allow an X-ray tube 52 to be moved in planar motion substantially horizontal to the ground supporting the carriage 12. As is illustrated in FIGS. 1, 2A and 2B, the articulating X-ray tube support arm 30 comprises a first pivotable support appendage 36 having a first end (not shown) engaged with the mast 20 at the front side 21 and a second end 32. The engagement of the first pivotable support appendage 36 with the mast will be discussed more fully below. A second pivotable support appendage 40 also has a first end 41 and a second end 42. The first end 41 of the second pivotable support appendage 40 is pivotally coupled to the second end 38 of the first pivotable support appendage 36. The articulating X-ray tube support arm 30 also includes a third pivotable support appendage 44 having a first end 45 and a second end 46 and a fourth pivotable support appendage 48 also having a first end 49 and a second end 50. The first end 45 of the third pivotable support appendage 44 is pivotally coupled to the second end 42 of the second pivotable support appendage 40 while the second end 46 of the third pivotable support appendage 44 is pivotally coupled to the first end 49 of the fourth pivotable support appendage 48. The X-ray tube 52 is connected to the second end 50 of the fourth pivotable support appendage 48 via a trunnion clamp 54 having a first hoop 55a and a second hoop 55b. Hoops 55a and 55b have aligned radial slots 53a and 53b. A detailed description of the pivotal couplings connecting the appendages of the X-ray tube support arm 30 follows below.

Referring now to FIGS. 1 through 4C, a pair of rectangular X-ray tube skin guards comprising a left guard 56a and a right guard 56b are attached to the X-ray tube 52 by well known and ordinary means. Right guard 56b also includes a handle portion 59. X-ray tube guards 56a and 56b, as well as handle 59, provide an operator with a means for positioning the X-ray tube 52 along the horizontal plane as well as allow the operator to rotate the X-ray tube 52 relative to the trunnion clamp 54 from a first position as shown by the numeral 57 to a second position shown as 58. The ordinary skin guards 56a and 56b also serve to protect the collimator assembly (not shown) of the X-ray tube 52 from damage caused by impact as well as ensure that the collimator cannot be placed any closer to the skin than the minimum source to skin distance (SSD), usually 30 cm, permitted by the FDA.

Figure 3A:
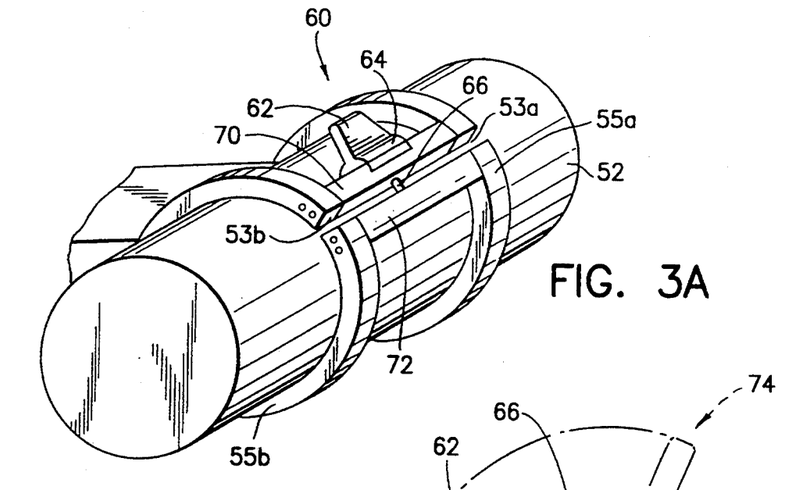
FIG. 3A which is a perspective view of the trunnion clamp supporting the X-ray tube.
Figure 3B:
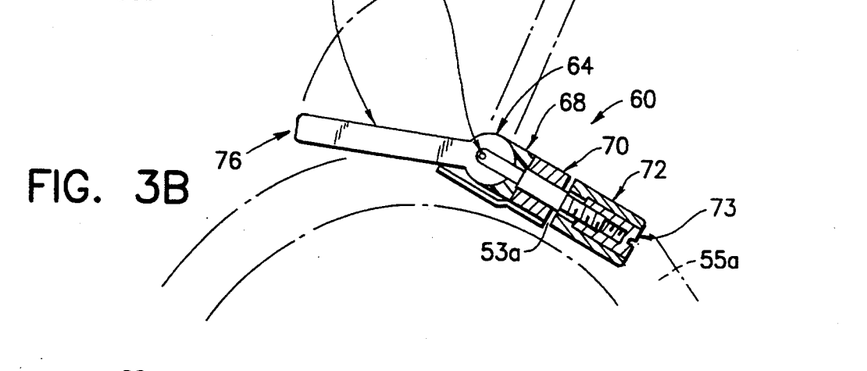
FIG. 3B which is a cross-sectional view of the trunnion clamping mechanism.
Figure 3C:
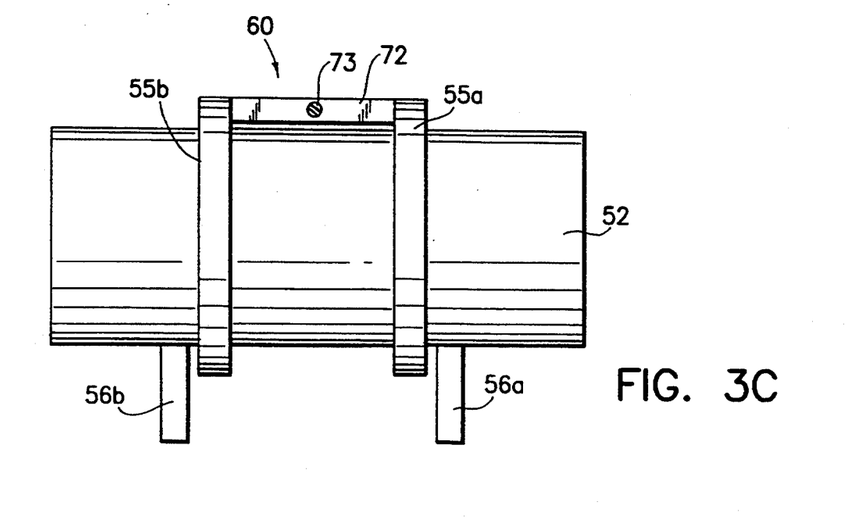
FIG. 3C which is a front view of the trunnion clamp supporting the X-ray tube.
Figure 4A:
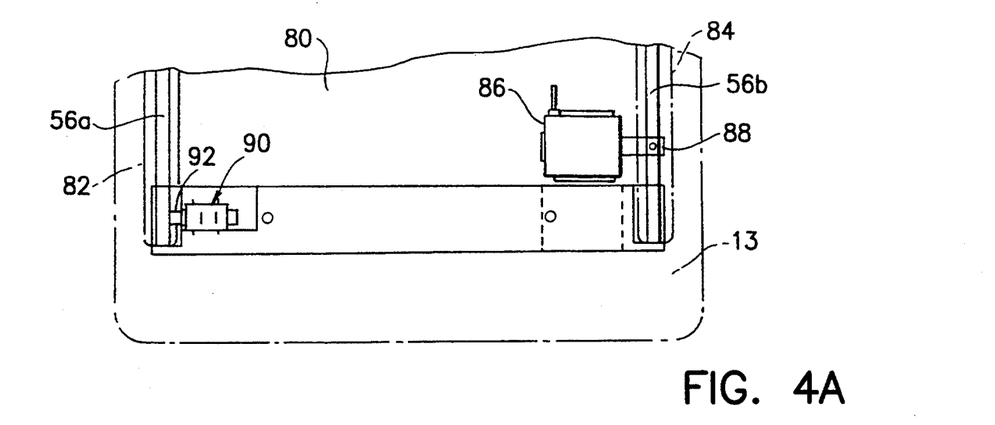
FIG. 4A which is a top view of the X-ray tube being locked into the cradle of the improved mobile X-ray apparatus carriage.
Figure 4B:
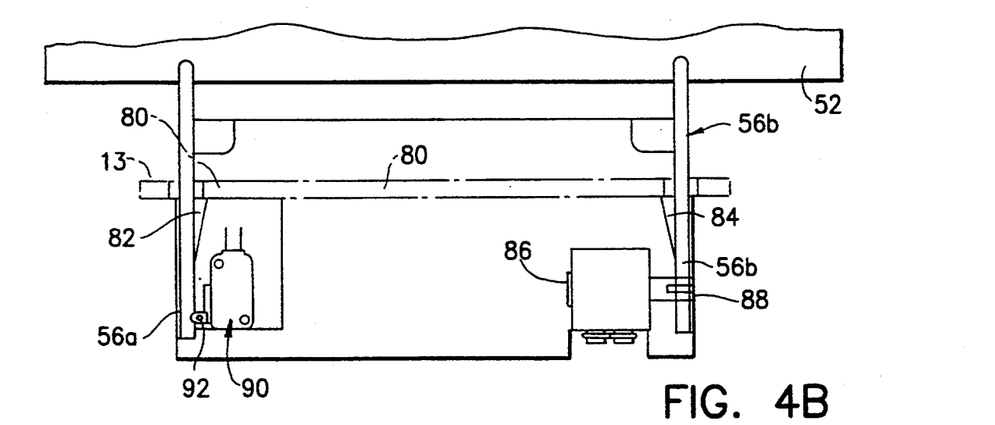
FIG. 4B which is a front view of the X-ray tube being locked into the cradle; of the improved mobile X-ray apparatus carriage.
Figure 4C:
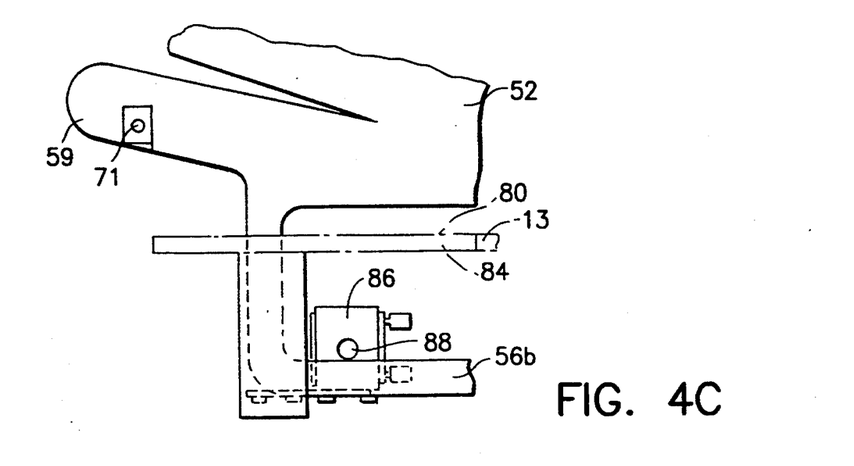
FIG. 4C which is a side view of the X-ray tube being locked into the cradle of the improved mobile X-ray apparatus carriage.

As shown in FIGS. 3A through 3C, the trunnion clamp 54 includes a "quick release" type lever and cam locking system as generally indicated by the numeral 60. The lever and cam locking system 60 generally comprises a first and second block 70 and 72 respectively attached between trunnion hoops 55a and 55b. As is shown by FIG. 3A, first block 70 is attached to hoops 55a and 55b on one side of aligned slots 53a and 53b while second block 72 is attached to hoops 55a and 55b on the other side of slots 53a and 53b. Clamping of the X-ray tube 52 is accomplished by drawing first and second blocks 70 and 72 together causing hoops 55a and 55b to become constricted. First and second blocks 70 and 72 are drawn together by tensioning of an over center pin 66 anchored at one end in the second block 72 by a tension adjusting screw 73. Tension on the over center pin 66 is established by the force of cam 64 and lever 62 connected to the over center pin 66 on a Delrin TM bearing surface 68 adjacent to first block 70. When lever 62 is in an open position as generally illustrated by the numeral 74, the X-ray tube 52 may be rotated within the trunnion hoops 55a and 55b because the hoops are in an unconstricted state and their unconstricted state diameter is larger than that of the X-ray tube 52. When lever 62 is in a closed position as generally illustrated by the numeral 76, the X-ray tube 52 may not be rotated due to the pressure exerted on the tube 52 by hoops 55a and 55b when the hoops are constricted. The lever and cam locking system 60 thereby provides a quick and convenient means for locking and unlocking the X-ray tube 52 so that the X-ray tube 52 may be precisely rotated by the operator with guards 56a and 56b or handle 59 and then locked in a predetermined position.

Now referring to FIGS. 1, 2A, 2B and 4A through 4C, the top portion 13 of the carriage 12 includes an X-ray tube cradle 80 having first and second slots 82 and 84 therein. Below cradle 80 adjacent to slot 84 there is located a solenoid 86 with associated plunger 88 which is of sufficient length to extend substantially across slot 84 when the solenoid is deenergized. The body of a limit switch 90 is positioned below cradle 80 adjacent to slot 82 such that a portion of a tripping means 92 of the limit switch 90 may extend into slot 82.

As will be appreciated by those skilled in the art, the four pivotable support appendages of the articulating X-ray tube support arm 30, the function of which has been previously discussed, permits the X-ray tube 52 to be pivoted in a manner such that the guards 56a and 56b may be aligned with and placed into slots 82 and 84 of cradle 80. When guards 56a and 56b are positioned deep enough within slots 82 and 84 as determined by the contact of guard 56a with protruding tripping means 92 thereby closing limit switch 90, the X-ray tube 52 may be locked in cradle 80 by de-energizing solenoid 86 so that plunger 88 extends substantially across slot 84 when a portion of guard 56b is located below the plunger 88. Also, limit switch 90 may be connected to the general X-ray control circuits (not shown) so as to disable the X-ray tube when contact is made between guard 56a and tripping means 92. When the X-ray tube 52 is locked in the cradle 80, the risk of damage to the X-ray tube 52 caused by inadvertent movement of the tube 52 during maneuvering of the carriage 12 is lessened. As will be more fully discussed below, the articulating X-ray tube support arm 30 may also be locked into its resting position as well as any other desired position by a plurality of electromagnetic brakes positioned within the plurality of X-ray tube support arm appendages 36, 40, 44 and 48. An example of such means between two appendages is shown in FIG. 5.

Figure 5:
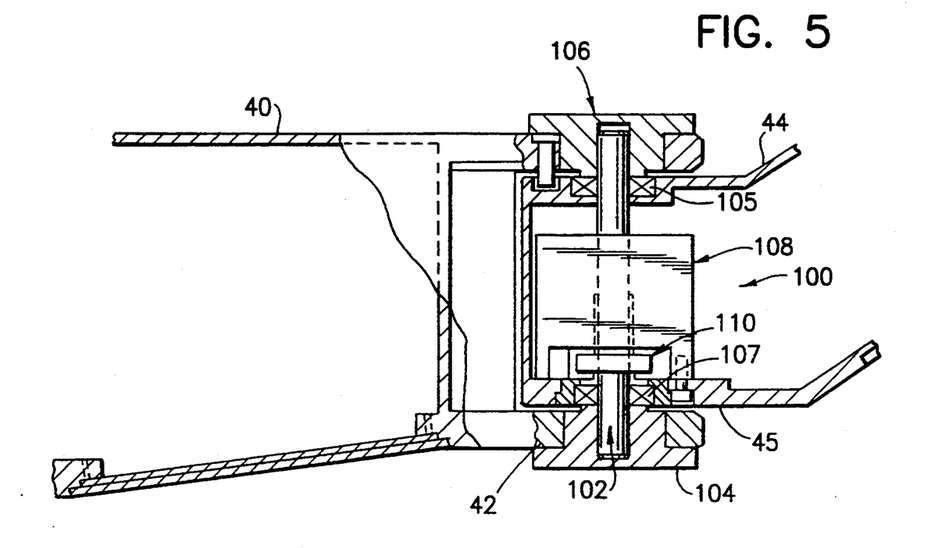
FIG. 5 which is a side view of a portion of the articulating X-ray tube support arm principally illustrating the electro-magnetic multi-disc braking system for preventing relative pivoting of adjacent support arm appendages.

Now referring to FIG. 5, a portion of second pivotable support appendage 40 and position of third pivotable support appendage 44 are shown pivotally coupled by a shaft 102 which is secured to the second end 42 of second pivotable support appendage 40 by first and second end caps 104 and 106 respectively. Smooth rotation of the third pivotable support appendage 44 about shaft 102 is provided by bearing sets 105 and 107 positioned between the third pivotable support appendage 44 and first and second end caps 104 and 106 attached to second pivotable support appendage 40. As shown in FIG. 5, an ordinary electromagnetically actuatable multi-disk brake 100 with housing 108 is positioned about shaft 102 and within the first end 45 of the third pivotable support appendage 44. The multi-disk brake housing 108 is attached to the third pivotable support appendage 44. A clamp collar 110 secures multi-disk brake 100 to shaft 102. When no power is applied to brake 100, a spring (not shown) within the brake forces the multiple disks to make contact thereby preventing pivoting movement of the third pivotable support appendage 44 relative to the second pivotable support appendage 40. When power is applied to the electro-magnetic brake 100, the electro-magnetic force acts against the spring to allow decoupling of the multiple disks and thereby allow movement of the two adjacent pivotable support appendages 40 and 42. Similar electro-magnetic brakes may be positioned at the pivot points of all of the pivotable support appendages of the articulating X-ray tube support arm 30 to prevent movement thereof. An ordinary electro-magnetic actuated multi-disk brake supplied by Inertia Dynamics has been found to perform satisfactorily for the purposes of immobilizing the articulating X-ray tube support arm 30 of the present invention. A switch 71 located on handle 59 electrically connected in an ordinary manner to the brakes may be used to activate or deactivate them as well as activate or deactivate solenoid 86. As will be readily appreciated by those skilled in the art, the use of a brake with single or multiple disks in the practice of the present invention will not deviate from its scope.

Figures 6A, 6B, 6C:
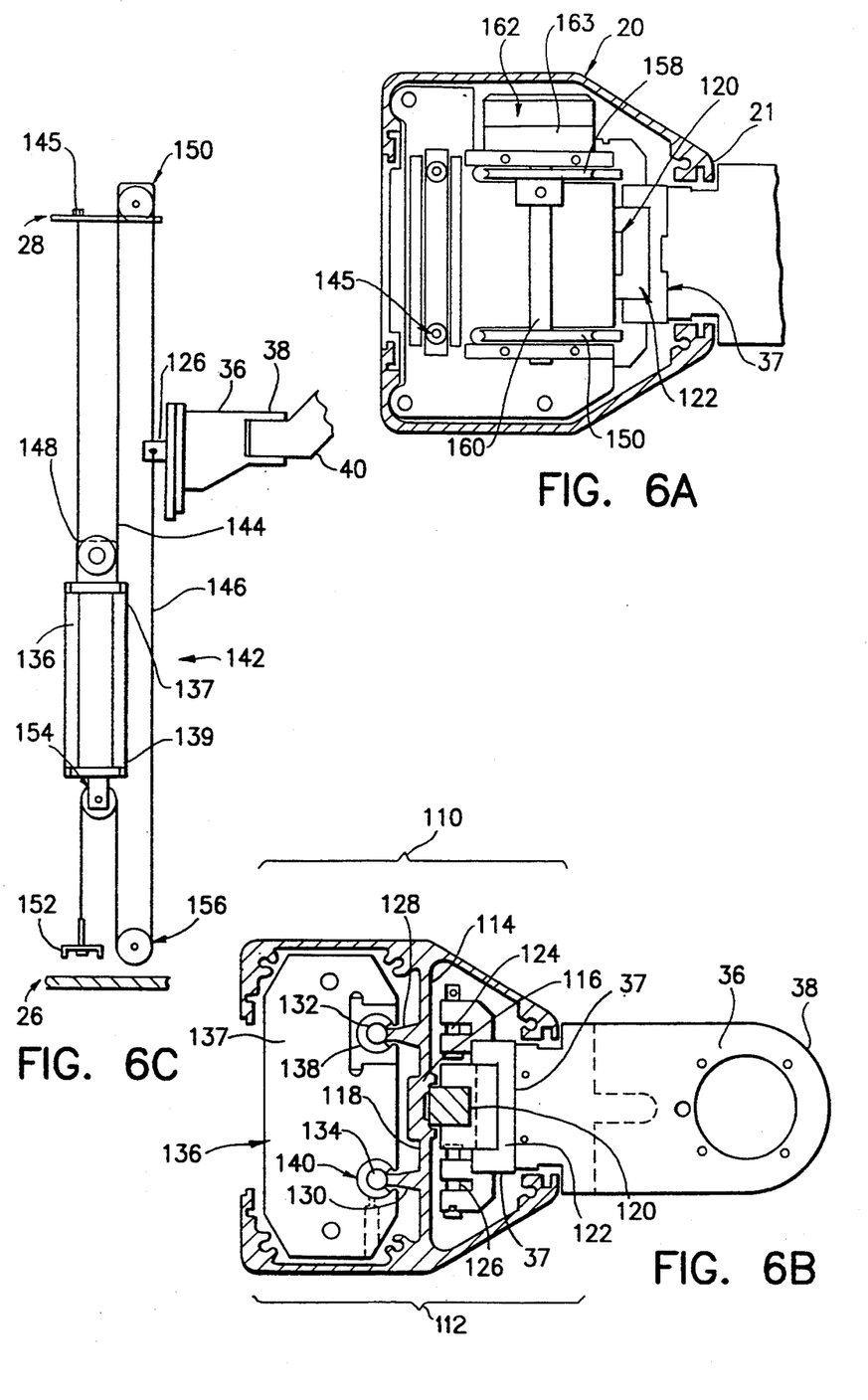
FIG. 6A which is a view of the interior of the top of mast of the improved mobile X-ray apparatus principally illustrating a pulley arrangement.
FIG. 6B which is a cross-sectional view of the mast of the improved mobile X-ray apparatus principally illustrating the rail system for engaging the articulating arm and counterweight therein.
FIG. 6C which is a schematic view of the counterweighting system within the mast of the improved mobile X-ray apparatus.

FIGS. 1 and 6A through 6C illustrate the inner workings of the mast 20 and the attachment of the first pivotable support appendage 36 thereto. Referring to FIG. 6B wherein the mast 20 is shown in a sectional view, it may be seen that mast 20 is formed as a single extrusion and comprises a first flange 110, a second flange 112 and a web 114, having a first side 116 and a second side 118 connecting the first flange 110 to the second flange 112 much like an 1-beam. Of course, it is not necessary for the purposes of the present invention that mast 20 be formed from a single extrusion provided that the mast 20 generally have a pair of flanges and a web as discussed above. A first rail 120, also shown in section, is attached to the first side 116 of web 114. The first rail 120 substantially extends from the first end 26 to the second end 28 of the mast 20. As shown by FIG. 6B, the first end 37 of pivotable support appendage 36 is coupled to rail 120 by a coupling 122 having a plurality of bearings (not shown) surrounding the rail 120. Coupling 122 permits the first pivotable support appendage 36 and of course the articulating X-ray tube support arm 30, to slide along the mast 20 between the first and second ends 26 and 28 respectively. As will be explained more fully below, coupling 122 may also include a pair of cable anchoring pins 124 and 126 for securing cables to the first pivotable support appendage 36.

The second side 118 of web 114 also includes first and second rail support members 128 and 130 extending outwardly therefrom. A pair of rails 132 and 134 are attached to the first and second rail support members 128 and 130. A counterweight 136 is slideably coupled to the rails 132 and 134 by set of couplings containing bearings (not shown) located at the top 137 of counterweight 136 as well as at the bottom 139. FIG. 6B illustrates slidable coupling 138 and 140 located at the top 137 of counterweight 136 connecting the counterweight to rails 132 and 134. Bearings in couplings 138 and 140 allow the counterweight 136 to freely slide substantially along the entire length of the mast 20 from the first end 26 to the second end 28. The couplings located at the bottom 139 of counterweight 136 are arranged in a similar manner to that shown for couplings 138 and 140 in FIG. 6B. Thus, as can be understood by those skilled in the art, the four counterweight couplings slideably secure the counterweight 136 to rails 132 and 134.

Figure 7A:
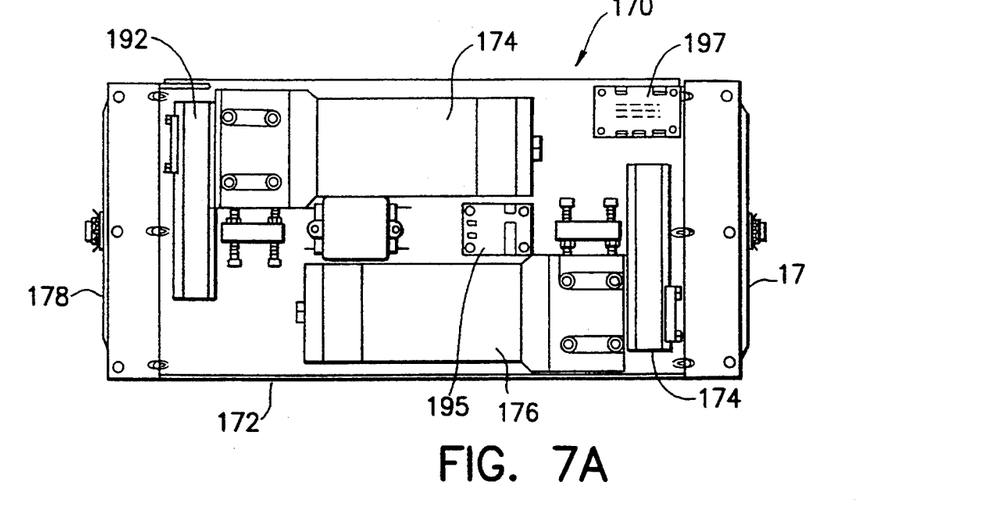
FIG. 7A which is a top view of the drive carriage of the improved mobile X-ray apparatus, principally illustrating the relative positioning of the motors.
Figure 7B:
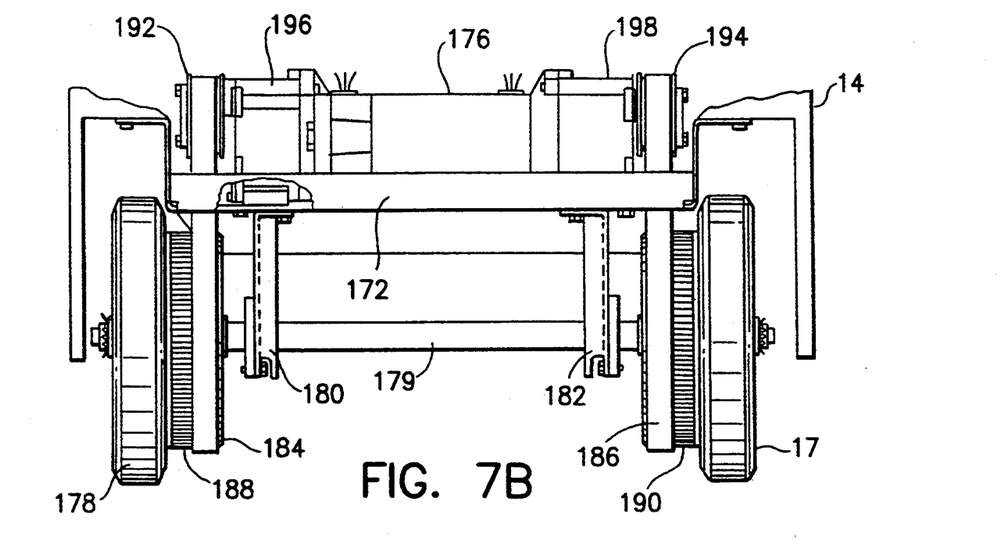
FIG. 7B which is a front view of the drive carriage of the improved mobile X-ray apparatus, principally illustrating the drive train for rotating the driven wheels.
Figure 8:
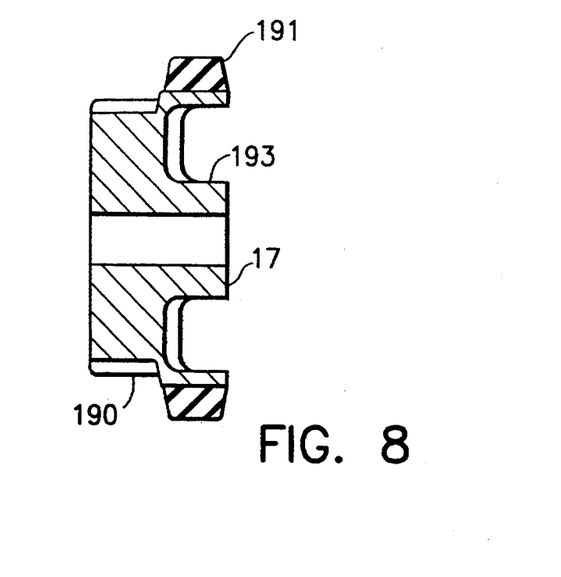
FIG. 8 which is a cross-sectional view of a driven wheel utilized in the improved mobile X-ray apparatus.

A counterweight system 142 for counterweighting the movement of the first pivotable support appendage 30 along the mast 20 is shown in FIG. 6C. Now referring to FIGS. 6A through 6C, according to the present invention the first pivotable support appendage 30 may be counterweighted by connection to the counterweight 136 by a first cable 144 and a second cable 146. One end of first cable 144 is attached to anchor 145 located at the second end 28 of the mast 20. The first cable 144 is routed through an upper counterweight pulley 148 and an upper mast pulley 150 before the other end of the first cable 144 is attached to the first pivotable support appendage 30 at a cable anchor 124. Likewise, one end of the second cable 146 is secured to anchor 152 located at the first end 26 of mast 20, and the second cable 146 is routed through lower counterweight pulley 154 and lower mast pulley 156 before its other end is attached to cable anchor 124 of the first pivotable support appendage 20. Referring to FIG. 6A, an additional upper mast pulley 158 is shown attached to a shaft 160 which is, in turn, connected to upper mast pulley 150. Additional counterweight pulleys and an additional lower mast pulley may be used to guide additional cables in a similar manner to that described for first and second cables 144 and 146. The additional cables provide redundancy as well as more uniform movement of the counterweight 132 and X-ray tube support arm 30. Also shown on FIG. 6A is an electromagnetic disk brake means 162 connected to shaft 160 that may be used in an ordinary manner to prevent the inadvertent raising and lowering of articulating X-ray tube support arm 30 along mast 20. In an alternative embodiment, an electric motor 163 may be used together with the brake 162 to raise and lower the articulating x-ray tube support arm 30 along mast 20. Now referring to FIGS. 7A, 7B and 8, the mobile X-ray apparatus 10 of the present invention is propelled along the floor of a hospital or other similar institution by drive subcarriage 170 attached to the base 14 of carriage 12. The drive sub-carriage comprises a platform 172 on which a pair of electric motors 174 and 176 are positioned so that they lay on the platform substantially between a left driven wheel 178 and the right driven wheel 17. The left and right driven wheels 178 and 17 are connected to the cart by axle 179 held in position by supports 180 and 182 extending downwardly from sub-carriage platform 172. Left and right driven wheels 178 and 17 are attached to the axle 179 in a manner that permits them to rotate independently from each other. The driven wheels 178 and 17 are propelled by motors 174 and 176. The propulsion is accomplished via toothed belts 184 and 186 that are connected between gear portions 188 and 190 of the wheels and toothed pulleys 192 and 194 of transmissions 196 and 198 coupled to the shafts of motors 174 and 176. The direction and magnitude of rotation of each of the wheels 178 and 17 may be independently controlled by associated motor speed and direction control circuits 195 and 197 of the type ordinarily associated with electric motor control. As shown in FIG. 8, the wheels 178 and 17 are preferably fabricated as single casting 193 that includes the gear portions 190 wherein a rubber wheel 191 is attached thereto. The single casting 193 ensures that there are fewer parts to assemble during the manufacturing process and also ensures fewer moving parts that could inadvertently become disassembled possibly causing damage or injury.

Now referring to FIGS. 2A, 2B, 7A, 7B and 9A through 9C, input to motor control circuits 195 and 197 is accomplished by placing a force on a handle 200 having first and second ends 202 and 204. The first and second ends 202 and 204 are positioned within large openings 205 and 207 of first and second projections 206 and 208 located at the rear portion of carriage 12. The openings 205 and 207 are made to be larger than the width of the handle 200 so as to allow some movement of the handle 200 relative to the carriage 12 when force is applied thereon by an operator. The movement of handle 200 relative to the carriage 12 is restrained by a resilient material 222, such as a dense cellular foam, fitted in the space between the opening 205 and first handle 202 and in the space between opening 207 and second handle end 204. The handle movement is also restrained by a pair of strain gage assemblies 210 and 212 located within each end 202 and 204 of handle 200. As shown by the sectional view of handle 200 in FIG. 9B, a first strain gage assembly 210 located at the first end 202 of handle 200 comprises a base 214 and beam 216 attached to the base 214. The base 214 is mounted within cavity 218 and beam 216 is permitted to extend past the first end 202 of handle 200 into opening 205 and an aperture 220 in the first projection 206 of carriage 12. The diameter of aperture 220 is intentionally made larger than that of beam 216 so the beam 216 is permitted to have some free play within the aperture 220. Likewise, the second strain gage assembly 212 is located at the second end 204 of handle 200. Similarly, the second strain gage assembly 212 comprises a base 224 and a beam 226 attached to the base 224. Base 224 is mounted within cavity 228 so that beam 226 is permitted to extend past the second end 204 of handle 200 into opening 207 and an aperture 230 in the second projection 208 of carriage 12. The diameter of aperture 230, similar to the diameter of aperture 220, is intentionally made larger than that of beam 226. The resilient material 222 together with apertures 220 and 230 allow beams 216 and 226 to deflect when contact is made with apertures 220 and 230 but prevent over-deflection and possible binding thereof. The resilient material 222 also bias the handle 200 to a neutral position so that when no force is applied to handle 200 the beams of strain gage assemblies 210 and 212 are not deflected and thereby no signals are sent by the strain gage assemblies to the control circuits 195 and 197. Over-deflection of prior art strain gage handle and carriage assemblies of different design has been known to cause binding which in turn causes the driven wheels to be inadvertently propelled although the force causing the over-deflection and binding had been removed. The interface between the handle 200, strain gage assemblies 210 and 212 and carriage 12 of the present invention alleviates the problems associated with binding.

Figure 10:
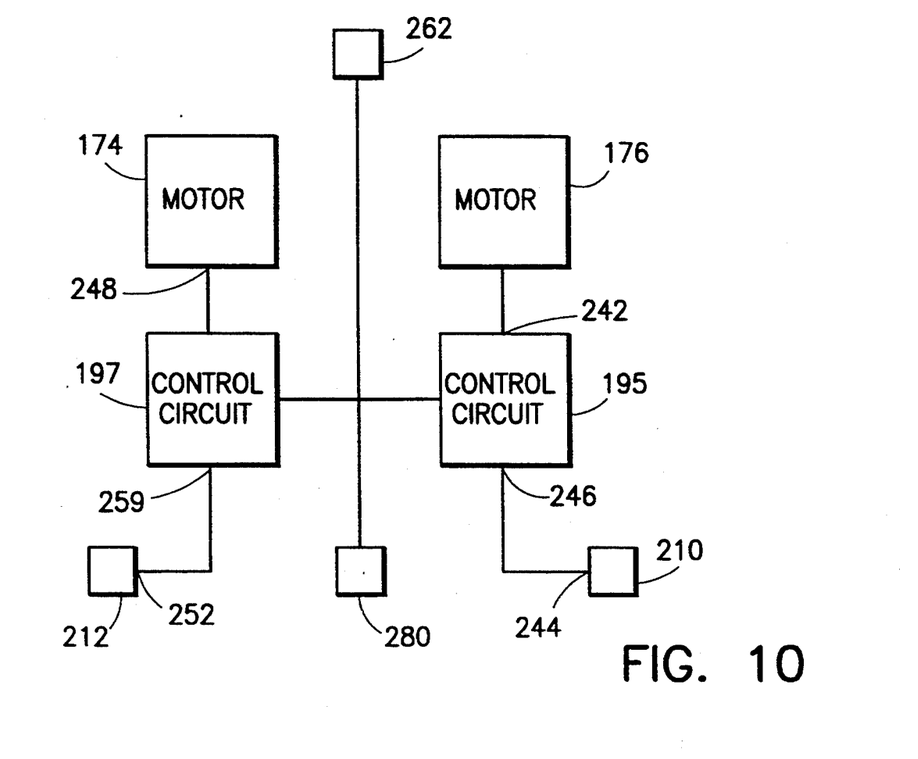
FIG. 10 which is a schematic diagram of the motor drive control circuits.

As will be appreciated by those skilled in the art, both strain gage assemblies 210 and 212 sense the direction and magnitude of relative force placed on handle 200 and appropriately send output signals to the motor speed and direction control circuits 195 and 197. Referring to FIG. 10, according to the present invention input 240 of electric motor 176 is connected to output 242 of control circuit 195 and output 244 of strain gage assembly 210 is connected to the input 246 of control circuit 195. Likewise, input 248 of electric motor 174 motor is connected to output 250 of control circuit 197 and output 252 of strain gage assembly 212 is connected to input 254 of control circuit 197. Because both strain gage assemblies 210 and 212 are mounted to the handle 200 and each are used to independently control the electric motors 174 and 176, the operator of the mobile X-ray apparatus 10 may virtually control the movement of the apparatus 10 with one hand placed near the middle of the handle 200.

Referring to FIGS. 1 and 10, a bumper 260 is positioned at the front 11 of carriage 12. Bumper 260 is attached to a safety cutoff switch 262 that is electrically connected to motor control circuits 195 and 197. Should the bumper 260 strike an obstruction, the switch 262 automatically stops and prevents further forward motion of the drive motors 174 ;and 176 through control circuits 195 and 197. Reverse motion is neither stopped nor prevented by switch 262 so that the apparatus 10 may be backed away from the obstruction.

Figures 9A, 9B:
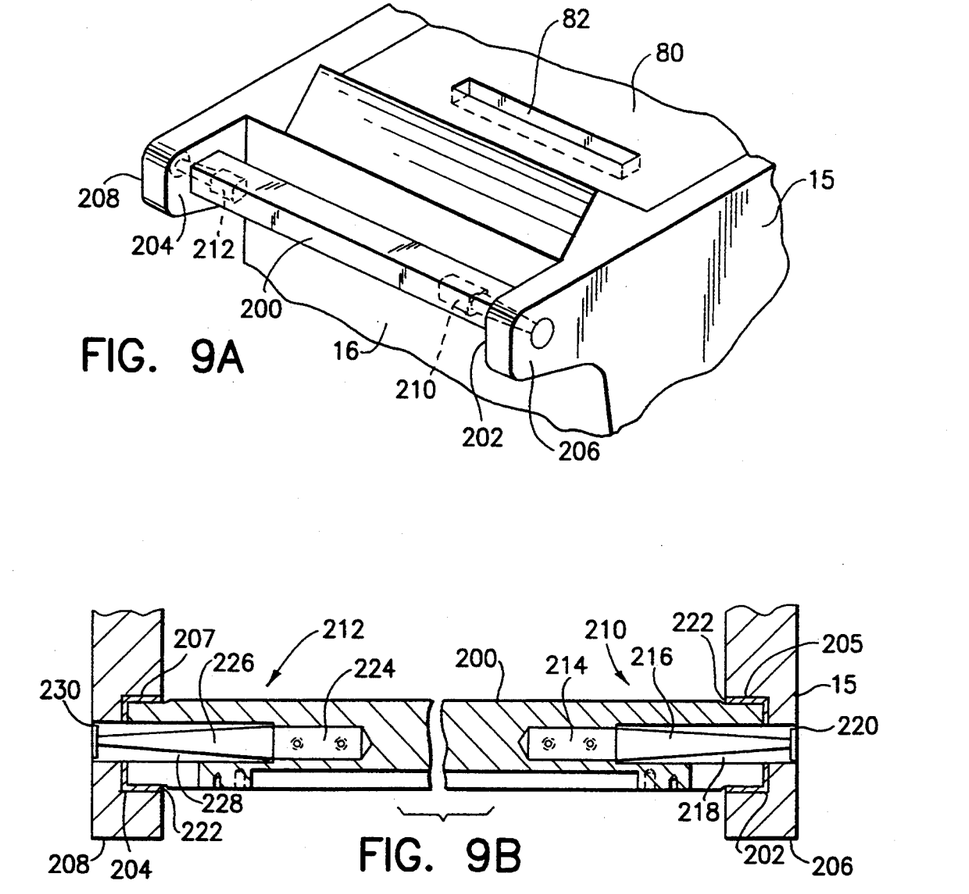
FIG. 9A which is a perspective view of a portion of the carriage of the improved mobile X-ray apparatus further illustrating the support of the handle by a pair of strain gage assemblies.
FIG. 9B which is a top cross-sectional view of the end of the handle illustrating the supporting strain gage assembly engaged with the carriage.
Figure 9C:
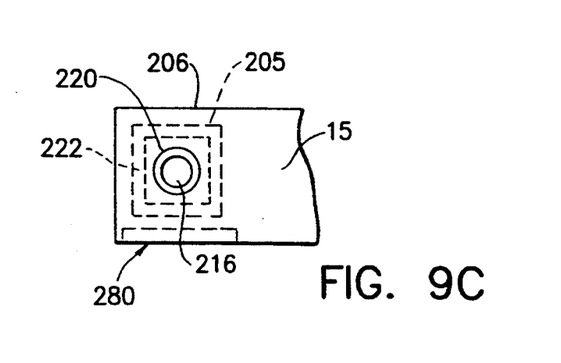
FIG. 9C which is a side view of the carriage illustrating the engagement of the strain gage with the carriage.

Referring to FIG. 1, 9C and 10, in an alternative embodiment, handle 200 includes brake switch 280 which, when depressed, enables strain gage assemblies 210 and 212 to be responsive to forces applied to handle 200 and thereby allowing control circuits 195 and 197 to propel wheels 178 and 17. When brake switch 280 is not depressed, strain gage assemblies 210 and 212 remain unresponsive to the forces applied to handle 200. Brake switch 280 provides a safety system which prevents inadvertent carriage movement that would otherwise result from unintentional contact with handle 200.

Although the present invention has been described with respect to one or more particular embodiments of the apparatus, it will be understood that other embodiments of the present invention may be made without departing from the spirit and scope of the present invention. Hence, the present invention is deemed limited only by the appended claims and the reasonable interpretation thereof.

What is claimed is:

1. An improved mobile X-ray apparatus comprising:
   a carriage having a base, a top, a front portion, a rear portion, and two opposed sides;
   a plurality of wheels, wherein the wheels are attached to and arranged about the base of the carriage so as to stably support the base from a floor;
   a mast having a first end and a second end, wherein the first end of the mast is fixedly attached to the carriage, and wherein the mast further comprises:
      a first flange;
      a second flange; and
      a web positioned between the first and second flanges, the web including a first side and a second side;
   a first rail attached to the first side of the web and extending substantially from the first end to the second end of the mast;
   a second rail attached to the second side of the web and extending substantially from the first end to the second end of the mast;
   an X-ray tube support arm having a first end and a second end, the first end having means for slidable coupling with the first rail and the second end having means for supporting an X-ray tube;
   an X-ray tube attached to the X-ray tube support arm by the means for supporting an X-ray tube;
   a counterweight having a first end and a second end means for slidable coupling with the second rail; and
   a means for connecting the X-ray tube support arm with the counterweight so that the weight of the X-ray tube support arm is counterbalanced by the weight of the counterweight.

2. The improved mobile X-ray apparatus of claim 1, wherein the means for connecting the X-ray tube support arm with the counterweight further comprises:
   a first mast pulley attached to the mast at its second end;
   a second mast pulley attached to the mast at its first end;
   a first counterweight pulley attached to the first end of the counterweight;
   a second counterweight pulley attached to the second end of the counterweight;
   a first cable having a first end and a second end, wherein the first end is anchored to the second end of the mast, wherein the cable is routed through the first counterweight pulley and the first mast pulley, and wherein the second end of the cable is attached to the X-ray tube support arm; and
   a second cable having a first end and a second end, wherein the first end is anchored to the first end of the mast, wherein the cable is routed through the second counterweight pulley and the second mast pulley, and wherein the second end of the cable is attached to the X-ray tube support arm.

3. An improved mobile X-ray apparatus comprising:
   a carriage having a base, a top, a front portion, a rear portion, a first side, a second side, the rear portion also including:
      a first projection located adjacent to the first side of the carriage, and wherein the first projection has an aperture therein;
      a second projection located adjacent to the second side of the carriage, and wherein the second projection has an aperture therein;
   a plurality of wheels attached to and arranged about the base so as to stably support the base from a floor, wherein the plurality of wheels including a first driven wheel and second driven wheel being arranged essentially at the rear portion of the base, the first wheel being positioned adjacent to the first side and the second wheel being positioned adjacent to the second side;
   means for controlling the rotation of the first driven wheel;
   means for controlling the rotation of the second driven wheel;
   a handle, the handle having:
      a first end including a cavity therein;
      a second end also including a cavity therein; wherein the first and second ends of the handle are positioned between the first and second projections of the rear portion of the carriage, the handle also including:
      a first strain gage having a beam and a base, wherein the first strain gage is electrically connected to the means for controlling the rotation of the first driven wheel so as to provide the means with electrical signals representative of the magnitude and direction of deflection of the beam of the first strain gage, wherein the base of the first strain gage is rigidly attached to the handle within the cavity of the first end of the handle, and wherein the first strain gage beam is permitted to extend outwardly past the first end of the handle and into the aperture of the first projection of the rear portion of the carriage;
      a second strain gage having a beam and a base, wherein the second strain gage is electrically connected to the means for controlling the rotation of the second driven wheel so as to provide the means with electrical signals representative of the magnitude and direction of deflection of the beam of the second strain gage, wherein the second strain gage base is rigidly attached to the handle within the cavity of the second end of the handle, and wherein the second strain gage beam is permitted to extend outwardly past the second end of the handle and into the aperture of the second projection of the rear portion of the carriage;
   a mast, the mast having a front side, a back side, two opposed sides, a first end attached to the base of the carriage, and a second end;
   an articulating X-ray tube support arm having a first end engaged with the front side of the mast so as to allow the X-ray tube support arm to slide along the front side and a second end having means for supporting an X-ray tube attached thereto; and an X-ray tube connected to the means for supporting an X-ray tube attached to the second end of the articulating X-ray tube support arm.

4. The improved mobile X-ray apparatus of claim 3, wherein the first driven wheel comprises a single casting having an axial bore therethrough, wherein a portion of the casting includes a plurality gear teeth and the remaining portion of the casting is surrounded by a dense resilient material, and wherein the second driven wheel comprises a single casting having an axial bore therethrough, wherein a portion of the casting includes a plurality gear teeth and the remaining portion of the casting is surrounded by a dense resilient material.

5. The improved mobile X-ray apparatus of claim 3, wherein the means for controlling the rotation of the first driven wheel comprises a first motor and first motor speed control circuit, the first motor being coupled to the first driven wheel by a first drive belt, wherein the means for controlling the rotation of the second driven wheel comprises a second motor and second motor speed control circuit, the second motor being coupled to the second driven wheel by a second drive belt, and wherein the first and second motors are positioned on the base of the carriage between the first and second driven wheels.

6. The improved mobile x-ray apparatus of claim 3, further including a bumper switch attached to the front portion of the carriage, the bumper switch being electrically connected to the means for controlling the rotations of the first driven wheel and the means for controlling the second driven wheel, the bumper switch being responsive to contact such that upon such contact motion in a forward direction is temporarily terminated while motion in a rearward direction is not terminated.

7. The improved mobile X-ray apparatus of claim 3, wherein the handle further includes a switch electrically connected to the first and second strain gages whereby when the switch is depressed the first and second strain gages are rendered responsive to force applied thereon and whereby when the switch is not depressed the first and second strain gages are rendered unresponsive to forces applied thereon.

* * * * *